(12) United States Patent
Krumme

(10) Patent No.: US 6,776,999 B1
(45) Date of Patent: Aug. 17, 2004

(54) EXPANDABLE GASTRORETENTIVE THERAPEUTICAL SYSTEM WITH PROLONGED STOMACH RETENTION TIME

(75) Inventor: Markus Krumme, Neuwied (DE)

(73) Assignee: LTS Lohmann Therapie-Systeme AG, Andernach (DE)

(*) Notice: Subject to any disclaimer, the term of this patent is extended or adjusted under 35 U.S.C. 154(b) by 0 days.

(21) Appl. No.: 09/830,533

(22) PCT Filed: Oct. 23, 1999

(86) PCT No.: PCT/EP99/08043

§ 371 (c)(1),
(2), (4) Date: Apr. 26, 2001

(87) PCT Pub. No.: WO00/25742

PCT Pub. Date: May 11, 2000

(30) Foreign Application Priority Data

Oct. 30, 1998 (DE) .......................................... 198 50 309

(51) Int. Cl.⁷ .............................. A61K 9/48; A61K 9/16
(52) U.S. Cl. ...................... 424/451; 424/456; 424/457; 424/458; 424/466; 424/489; 424/490; 424/492
(58) Field of Search ................................ 424/451, 452, 424/456, 457, 458, 489, 490, 492, 466

(56) References Cited

U.S. PATENT DOCUMENTS

| | | | |
|---|---|---|---|
| 3,901,232 A | * | 8/1975 | Michaels et al. ............ 128/260 |
| 4,036,228 A | | 7/1977 | Theeuwes |
| 4,083,951 A | | 4/1978 | Goudie et al. |
| 4,207,890 A | * | 6/1980 | Mamajek et al. ............ 128/223 |
| 4,235,236 A | | 11/1980 | Theeuwes |
| 4,702,918 A | | 10/1987 | Ushimaru et al. |
| 4,758,436 A | | 7/1988 | Caldwell et al. |
| 4,767,627 A | * | 8/1988 | Caldwell et al. ............ 424/426 |
| 4,844,905 A | * | 7/1989 | Ichikawa et al. ........... 424/451 |
| 4,996,058 A | * | 2/1991 | Sinnreich .................... 424/462 |

FOREIGN PATENT DOCUMENTS

| | | | |
|---|---|---|---|
| EP | 0 121 331 A2 | 10/1984 | |
| EP | 0 147 780 A2 | 7/1985 | |
| EP | 0 307 904 A1 | 3/1989 | |
| FR | 2 323 440 | 4/1977 | |
| FR | 2323440 | * 7/1977 | ................. 128/260 |
| JP | 62207209 A | 9/1987 | |

OTHER PUBLICATIONS

Abstract of Int. J. Pharm., vol. 35, pp. 157–164 (1987).
Abstract of Chem. Pharm. Bull (Tokyo), vol. 33 (12); pp. 5495–5502 (1985).
Abstract of Dtsch. Med. Wochenschr. (Germany), vol. 106 (36), pp. 1143–1147 (1981).

* cited by examiner

Primary Examiner—Thurman K. Page
Assistant Examiner—Rachel M. Bennett
(74) Attorney, Agent, or Firm—Frommer Lawrence & Haug LLP

(57) ABSTRACT

The invention relates to a device for delaying the pylorus passage of orally administered medicament forms. Said device comprises a component which expands upon contact with the gastric juice and a polymer coat which is permeable to liquids but not to gases. The device can contain an active substance whose release into the gastric juice is mainly controlled by the medicament form into which it is incorporated. Unlike conventional medicament forms with delayed pylorus passage, the release of the active substance does not so much depend on the kind and structure of the polymer coat but is mainly determined by the incorporated medicament form. The inventive device can be easily rolled or folded and can be filled into capsules.

14 Claims, 1 Drawing Sheet

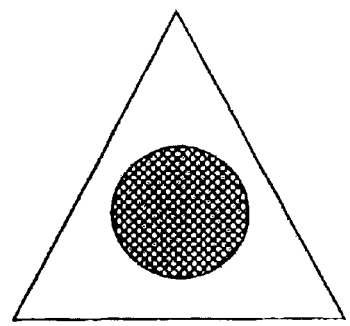
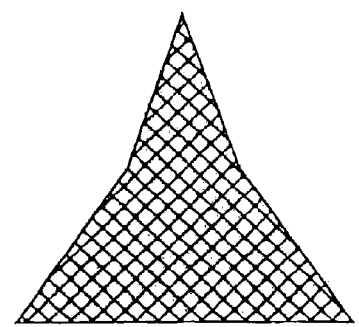
FIG. 1
FIG. 2
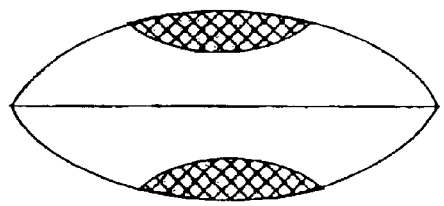
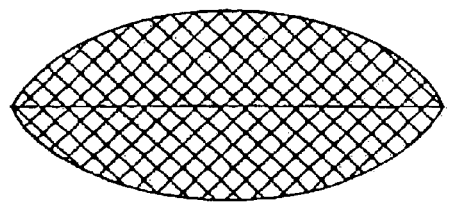
FIG. 3
FIG. 4
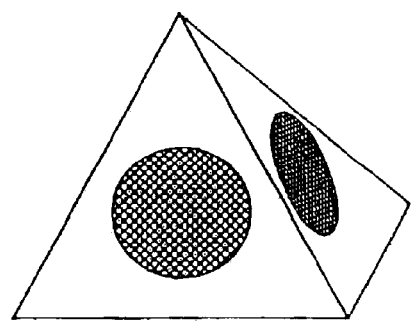
FIG. 5

EXPANDABLE GASTRORETENTIVE THERAPEUTICAL SYSTEM WITH PROLONGED STOMACH RETENTION TIME

This application is a 371 of PCT/EP99/08043 filed Oct. 23, 1999.

The present invention describes a device for delaying the pyloric passage of orally assimilable pharmaceutical forms having a component which is expandable on contact with gastric juice and a polymer coat which is permeable to liquids but gas-tight. The device can contain an active compound which is mainly released into the gastric juice in a controlled manner by the incorporated pharmaceutical form. Compared with conventional pharmaceutical forms having a delayed pyloric passage, the release of active compound is less dependent on the nature and composition of the polymer coat and is mainly determined by the incorporated form. The device according to the invention can be easily rolled or folded and can be filled into capsules.

U.S. Pat. No. 4,207,890 describes a device for the controlled release of active compounds, which due to its expansion undergoes local retention in the stomach and thereby has a prolonged residence time in the stomach. The device has (a) a polymer coat which is present in collapsed form before administration. The polymer coat itself has no openings and consists of a material which is virtually unhydratable, but is permeable to body fluids. The device additionally has (b) an element which controls the release of active compound. According to claim 2, this element can be the polymer coat itself. As a further element (c), the device has a component which is expandable in contact with body fluids.

The driving principle of the retentive action is osmosis, the element (c) being an osmotically active substance which drives water through the polymer coat (a) and thereby causes the formation of a solution in the device. The device will thus contain an aqueous solution in the expanded state and on account of the concentration conditions will make possible a diffusion of active compound from the device, but will correspond approximately to the chyme in its apparent density. The device will thus float or sink in the chyme. The retentive principle is exclusively the size of the device. A possible deflation mechanism is not described, thus removal of the device from the stomach and disposal after active compound administration is not elucidated.

A modification of the principle of retention is shown in EP 0 307 904 A1 and U.S. Pat. No. 4,996,058. Expandable components indicated are substances which, under admission of acid, form gaseous components such as carbon dioxide or nitrogen which inflate the polymer coat (a) and thus form a device which can be floated on the chyme. The principle of retention (see U.S. Pat. No. 4,996,058 column 3, lines 6 to 7) is floating on the chyme and thus the device is protected from emptying of the stomach through the pylorus. These devices have crucial disadvantages. In both cases, the control of the release of active compound essentially takes place through the polymer coat. At the same time, the inflation kinetics of the device are essentially limited by the polymer coat, as water and hydronium ions must diffuse through the polymer coat, but on the other hand active compound molecules must diffuse out in the opposite direction. The diffusion constant in the polymer coat is a crucial parameter. In the case of damage to the relatively thin and thus sensitive polymer coat by mechanical or chemical action, there is the danger of a sudden release of the active compound in the sense of dose-dumping. The extent of the expanding amount of gas produced depends, inter alia, strongly on the acidity of the environment and thus, however, on the composition of the chyme and the secretion of gastric acid. In the case of a strongly acidic environment and thus high gas production, the mechanical stress on the devices must not reach the bursting limit, on the other hand, in the case of a less acidic environment, an adequate production of gas must be achieved. This dilemma leads to highly variable states of the devices as a result of circadian variations in the gastric acidity.

The invention is therefore based on the object of making available a gastroretentive system which avoids these disadvantages of the systems known in the prior art.

According to the invention, these problems are solved by a gastroretentive device which contains the following elements:

(a) a polymer coat of microporous membrane or partially microporous membrane or a combination of both with another nonporous film-like polymer. The production of the pores can be carried out according to the invention by any desired process, e.g. by stretching of films, by use of multiphase systems and evaporation of a part of the system, by controlled polymerization, e.g. in the form of ionomers, by mechanical processes such as needling, by thermal processes such as lasers, or by irradiation with ionizing radiation and subsequent etching etc. Materials which can be used according to the invention for the microporous membrane are: polyurethanes, polypropylene, polyvinyl alcohol, polyvinyl acetate, polyacrylic acid and derivatives, polymethylmethacrylic acid and derivatives, polycarbonates, polyvinylidene difluoride, polytetrafluoroethylene and any other desired polymers which can be provided with pores of suitable size. According to the invention, the size of these pores is between 0.1 and 20 $\mu$m, preferably between 0.3 and 10 $\mu$m and particularly preferably between 0.5 and 1 $\mu$m. If appropriate, in order to make the pores better wettable, the membranes according to the invention can be impregnated with wetting agents or other hydrophilic components.

(b) an expandable component which produces a gas such as, for example, carbon dioxide or nitrogen on contact with gastric juice, in particular under the action of acid. Examples of these used according to the invention are, for example, carbonates and hydrogencarbonates of the alkali metals and alkaline earth metals, the ammonium cations or sodium azide or mixtures thereof. These expandable components can be optionally modified for the modification of the gas production kinetics, e.g. by coating with or embedding in lipophilic components such as waxes or fats or suitable coatings such as polymethacrylates or polymethylmethacrylates and derivatives or similar substances known to the person skilled in the art. According to the invention, the expandable component can also be foam-forming, e.g. as a result of the incorporation into polyvinyl alcohol, or in the form of a semisolid, ointment-like preparation, in order to control the deflation kinetics.

(c) a component containing the active compound such as, for example, multiparticulate preparations, tablets, capsules or semisolid, ointment-like preparations, or foams. Possible active compounds are fundamentally all substances having a physiological action, in particular pharmaceuticals for human or veterinary medicine, preferably those which are absorbed by the gastric mucosa or act on the surface of the gastric mucosa. Such pharmaceutical active compounds are known to the person skilled in the art. The components (b) and (c) can also be present in a joint preparation.

The device can be filled into a container made of physiologically acceptable material, for example into a hard gelatin capsule, in order to facilitate administration and handling.

The inflated form of the device is preferably that of an inflated triangle in order to have a planar structure of maximum bulk. Due to the planarity, in the state floating on the chyme, two preferred positions are stable which both allow passage of the chyme past the gastroretentive device such that the chyme cannot force the inflated form through the pylorus. Among the planar forms, the form of a triangle is a good compromise of bulkiness and stiffness of the structure in the inflated state and is therefore proposed for the retentive device. In the stomach, the bulky structure wedges between the stomach walls and allows the chyme to escape through the pylorus. The wedging in the lumen only has to withstand the flow resistance in the chyme. The more spherical the device, the more likely a bulb-like sealing of the stomach exit is conceivable, with the result that the emptying pressure forces the device through the pylorus. According to the invention, however, quadrangular and polygonal structures and also those having rounded corners can also be used.

As a result of the use of the microporous or porous polymer coat, according to the invention a number of problems can be solved. Owing to the surface tension of liquid, in particular aqueous systems, a certain pressure is necessary for the emptying of a liquid-filled pore, which essentially depends on pore diameter, surface tension and interfacial tension and the contact angle. By a suitable choice of the pore diameter, a defined pressure can be set for a given system, below which the pores cannot be emptied. The membrane is thus gas-tight. Liquids, however, can easily flow through the membrane; the flow is specified by the pore number and the dimensions of the pores and also the viscosity of the medium. By using microporous membranes of defined pore size, it is thus possible according to the invention to produce a device which is highly permeable to liquids, but impermeable to gases below a defined pressure. The internal pressure of the device is thereby limited to a prespecified value. On exceeding the pressure limit, the membrane becomes permeable and prevents, as a nondestructive safety device, mechanical stress on the device above the permissible bursting pressure. Thus it is possible with the device according to the invention to achieve an almost constant internal pressure over the period of use of the device. The period of use of the device is controllable by the nature and amount of the expandable component. By means of capillarity, particles lying on the inside of the membrane are wetted and release the active compound through the microporous membrane with only a small delay.

The systems according to the invention can be employed in human and veterinary medicine.

FIGURES

FIG. 1 shows the construction of a system according to the invention in plan.

FIG. 2 shows the construction of a further system according to the invention in plan.

FIG. 3 shows the side view of the system of FIG. 1

FIG. 4 shows the side view of the system of FIG. 2

FIG. 5 shows a gastroretentive system in tetrahedral form in perspective.

In the figures, cross-hatched areas correspond to the microporous membrane, non cross-hatched areas correspond to a nonporous polymer film. Because they are enclosed in the device, the components (b) and (c) are not visible.

What is claimed is:

1. A swallowable, gastroretentive device, which delays passage of the device through the pylorus of the stomach of an orally ingestable pharmaceutical form and releases at least one pharmaceutically active compound in a controlled manner, said device comprising:
   a) a pharmaceutical form which contains at least one pharmaceutically active compound;
   b) an expandable component which generates gas on contact with gastric juice; and
   c) a polymeric membrane system which totally encompasses components a) and b) above and is expandable by the gas generated by b) upon contact with the gastric juice, whereby the polymeric membrane system comprises at least one member selected from the group consisting of a microporous membrane, a porous membrane and a combination of any of the foregoing with a non-porous polymer film.

2. The device according to claim 1, wherein the size of the pores in the microporous or porous membrane is between 0.3 to 10 $\mu$m.

3. The device according to claim 1, wherein the size of the pores in the microporous or porous membrane is between 0.5 to 1 $\mu$m.

4. The device according to claim 1, wherein the microporous or porous membrane is permeable to liquids.

5. The device according to claim 1, wherein the microporous or porous membrane is impermeable to the gas generated by the expandable component on contact with the gastric juice.

6. The device according to claim 1, wherein the microporous or porous membrane is permeable to the gas generated by the expandable component on contact with the gastric juice when the internal pressure reaches defined pressure limit.

7. The device according to claim 1, wherein at least one pharmaceutically active compound in the pharmaceutical form or the expandable component is present in a semisolid form.

8. The device according to claim 1, wherein at least one pharmaceutically active compound in the pharmaceutical form or the expandable component is present in a multiparticulate preparation.

9. The device according to claim 1, wherein at least one pharmaceutically active compound in the pharmaceutical form or the expandable component is present in a foam-forming preparation.

10. The device according to claim 1, which further comprises a container made of a physiological acceptable material wherein said container contains the device.

11. The device according to claim 10, wherein the container is a hard gelatin capsule.

12. The device according to claim 1, wherein said device is in the form that is approximately planar triangular, planar tridentate, stellate or tetrahedral.

13. The device according to claim 12, wherein the polymeric membrane system is in a folded form that is fixed by a polymer coat that is soluble in gastric juice.

14. A swallowable, gastroretentive device, which delays passage of the device through the pylorus of the stomach of an orally ingestable pharmaceutical form and releases at least one pharmaceutically active compound in a controlled manner, said device comprising:
   a) a pharmaceutical form which contains at least one pharmaceutically active compound;
   b) an expandable component which generates gas on contact with gastric juice; and c) a polymeric membrane system which totally encompasses components a) and b) above and is expandable by the gas generated by b) upon contact with the gastric juice, whereby the polymeric membrane system comprises at least one member selected from the group consisting of a microporous membrane, a porous membrane and a combination of any of the foregoing with a non-porous polymer film, and the size of the pores in the microporous or porous membrane is between 0.1 to 20 µm.

* * * * *